US009453196B2

(12) United States Patent
Smith et al.

(10) Patent No.: US 9,453,196 B2
(45) Date of Patent: Sep. 27, 2016

(54) CELL CARRIER, METHODS OF MAKING AND USE

(75) Inventors: Reginald Donovan Smith, Schenectady, NY (US); Scott Michael Miller, Clifton Park, NY (US); Yosang Yoon, Green Island, NY (US); Slawomir Rubinsztajn, Ballston Spa, NY (US); Prameela Susarla, Houston, TX (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 894 days.

(21) Appl. No.: 13/287,611

(22) Filed: Nov. 2, 2011

(65) Prior Publication Data

US 2012/0156773 A1 Jun. 21, 2012

Related U.S. Application Data

(63) Continuation-in-part of application No. 12/970,735, filed on Dec. 16, 2010.

(51) Int. Cl.
*C12N 5/071* (2010.01)
*C12N 5/00* (2006.01)

(52) U.S. Cl.
CPC ......... *C12N 5/0068* (2013.01); *C12N 2533/12* (2013.01); *C12N 2533/30* (2013.01); *C12N 2535/10* (2013.01)

(58) Field of Classification Search
CPC .............. C12N 5/0068; C12N 5/0075; C12N 2533/12; C12N 2533/14; C12N 2533/30; C12N 2533/50; C12N 2535/00
USPC ................................. 435/395, 402
See application file for complete search history.

(56) References Cited

U.S. PATENT DOCUMENTS

| | | | |
|---|---|---|---|
| 4,801,475 A | 1/1989 | Halpern et al. | |
| 4,906,237 A | 3/1990 | Johansson et al. | |
| 5,284,766 A | 2/1994 | Okano et al. | |
| 5,449,620 A | 9/1995 | Khillan | |
| 5,707,859 A | 1/1998 | Miller et al. | |
| 5,763,548 A | 6/1998 | Matyjaszewski et al. | |
| 5,800,412 A | 9/1998 | Zhang et al. | |
| 6,121,371 A | 9/2000 | Matyjaszewski et al. | |
| 6,190,913 B1 * | 2/2001 | Singh ............................. | 435/394 |
| 6,627,314 B2 | 9/2003 | Matyjaszewski et al. | |
| 6,720,469 B1 | 4/2004 | Curtis et al. | |
| 6,777,227 B2 | 8/2004 | Ricci et al. | |
| 6,790,919 B2 | 9/2004 | Matyjaszewski et al. | |
| 6,861,103 B2 | 3/2005 | Chang et al. | |
| 7,052,776 B2 | 5/2006 | Fanta et al. | |
| 7,354,704 B2 | 4/2008 | Malin et al. | |
| 8,148,111 B2 | 4/2012 | Kurokawa et al. | |
| 8,241,907 B2 | 8/2012 | Shogbon et al. | |
| 2002/0028493 A1 | 3/2002 | de Bruijn et al. | |
| 2002/0081726 A1 | 6/2002 | Russell et al. | |
| 2003/0003554 A1 | 1/2003 | Miller et al. | |
| 2003/0036196 A1 * | 2/2003 | Okano et al. .................. | 435/373 |
| 2003/0162287 A1 | 8/2003 | Yamamoto et al. | |
| 2004/0214326 A1 | 10/2004 | Cousins et al. | |
| 2005/0054101 A1 | 3/2005 | Felder et al. | |
| 2006/0165625 A1 | 7/2006 | Verrall et al. | |
| 2006/0205071 A1 | 9/2006 | Hasson et al. | |
| 2008/0009064 A1 | 1/2008 | Ronfard et al. | |
| 2008/0026464 A1 | 1/2008 | Borenstein et al. | |
| 2008/0187995 A1 | 8/2008 | Murphy et al. | |
| 2008/0199959 A1 | 8/2008 | Algotsson et al. | |
| 2008/0208351 A1 | 8/2008 | Besenbacher et al. | |
| 2009/0047260 A1 | 2/2009 | Van Dyke | |
| 2009/0069904 A1 | 3/2009 | Picha | |
| 2009/0098183 A1 | 4/2009 | Detamore et al. | |
| 2009/0228027 A1 | 9/2009 | Yamanaka et al. | |
| 2009/0248145 A1 | 10/2009 | Chan et al. | |
| 2009/0248157 A1 | 10/2009 | Dalby et al. | |
| 2009/0311735 A1 | 12/2009 | Crook et al. | |
| 2010/0093053 A1 | 4/2010 | Oh et al. | |
| 2010/0124781 A1 | 5/2010 | Nelson | |
| 2010/0136647 A1 | 6/2010 | Algotsson et al. | |
| 2010/0197013 A1 | 8/2010 | Kamp et al. | |
| 2010/0291674 A1 * | 11/2010 | Beese et al. .................. | 435/325 |
| 2010/0304482 A1 | 12/2010 | Deshayes et al. | |

(Continued)

FOREIGN PATENT DOCUMENTS

DE 102006012960 A1 9/2007
EP 0382214 B1 8/1990

(Continued)

OTHER PUBLICATIONS

Fujita et al.; Time-lapse observation of cell alignment on nanogrooved patterns; Journal of the Royal Society Interface; vol. 6, S269-S277; published online Feb. 25, 2009.*
Search Report and Written Opinion from corresponding PCT Application No. PCT/EP2011/073065 dated Apr. 23, 2012.
Search Report and Written Opinion from corresponding PCT Application No. PCT/EP2011/073061 dated May 2, 2012.
Search Report and Written Opinion from corresponding PCT Application No. PCT/EP2011/073066 dated May 7, 2012.
Jae et al., "Time-dependent Modulation of Alignment and Differentiation of Smooth Muscle Cells Seeded on a Porous Substrate Undergoing Cyclic Mechanical Strain", Artificial Organs, vol. No. 30, No. 4, pp. 250-258, Apr. 1, 2006.
Jae et al., "Construction of Functional Soft Tissues From Premodulated Smooth Muscle Cells Using a Bioreactor System", Artificial Organs, vol. No. 30, No. 9, pp. 704-707, Sep. 1, 2006.

(Continued)

*Primary Examiner* — Antonio Galisteo Gonzalez
(74) *Attorney, Agent, or Firm* — Fletcher Yoder, P.C.

(57) ABSTRACT

A method of culturing adherent cells is provided, wherein the method comprises providing a carrier for growing the cells, comprising one or more surfaces; and one or more relief features/indentations are present on one or more of the surfaces, wherein the carrier has a length at least about 0.2 mm, a width at least about 0.2 mm, and a height in a range from about 0.012 mm to 0.5 mm; and wherein each of the relief features/indentations has a height above the surfaces in a range from about 2 to 200 μm, and width in a range from about 20 to 200 μm; seeding the cells on the carriers; and growing the cells on the carrier.

28 Claims, 10 Drawing Sheets

(56) References Cited

U.S. PATENT DOCUMENTS

| | | |
|---|---|---|
| 2010/0330674 A1 | 12/2010 | Rubinsztajn et al. |
| 2011/0027889 A1 | 2/2011 | McCarthy et al. |
| 2011/0076764 A1 | 3/2011 | Rubinsztajn et al. |
| 2011/0104732 A1 | 5/2011 | Lucic et al. |
| 2011/0129919 A1 | 6/2011 | Oh et al. |
| 2011/0160869 A1 | 6/2011 | Duch et al. |
| 2011/0207209 A1 | 8/2011 | Hammons et al. |
| 2011/0207216 A1 | 8/2011 | Martin et al. |
| 2011/0275154 A1 | 11/2011 | Martin et al. |
| 2012/0045830 A1 | 2/2012 | Green et al. |
| 2012/0052579 A1 | 3/2012 | Shannon et al. |
| 2012/0058556 A1 | 3/2012 | Fabian et al. |
| 2012/0058561 A1 | 3/2012 | Sato |
| 2012/0156772 A1 | 6/2012 | Miller et al. |
| 2012/0156773 A1 | 6/2012 | Smith et al. |
| 2012/0156777 A1 | 6/2012 | Rangarajan et al. |
| 2012/0219531 A1 | 8/2012 | Oh et al. |
| 2013/0034669 A1 | 2/2013 | Yoon et al. |
| 2013/0210140 A1 | 8/2013 | Burns et al. |
| 2014/0051163 A1 | 2/2014 | Healy et al. |
| 2014/0186946 A1 | 7/2014 | Davis et al. |
| 2014/0356949 A1 | 12/2014 | Davis et al. |

FOREIGN PATENT DOCUMENTS

| | | |
|---|---|---|
| EP | 1875234 B1 | 6/2011 |
| EP | 1874367 B1 | 7/2011 |
| GB | 1079391 A | 8/1967 |
| JP | 2004018556 A | 1/2004 |
| JP | 2010057485 A | 3/2010 |
| JP | 2010136706 A | 6/2010 |
| WO | 9932595 A1 | 7/1999 |
| WO | 0070406 A1 | 11/2000 |
| WO | 0162803 A2 | 8/2001 |
| WO | 0192359 A1 | 12/2001 |
| WO | 03055967 A1 | 7/2003 |
| WO | 2004090506 A3 | 10/2004 |
| WO | 2006033935 A2 | 3/2006 |
| WO | 2007125288 A1 | 11/2007 |
| WO | 2008106771 A1 | 9/2008 |
| WO | 2008140295 A1 | 11/2008 |
| WO | 2009034186 A1 | 3/2009 |
| WO | 2009105570 A2 | 8/2009 |
| WO | 2010094944 A1 | 8/2010 |
| WO | 2011106032 A1 | 9/2011 |
| WO | 2011147930 A1 | 12/2011 |
| WO | 2012069841 A1 | 5/2012 |

OTHER PUBLICATIONS

Liang-Ting et al., "Fabrication of plastic microlens arrays using hybrid extrusion rolling embossing with a metallic cylinder mold fabricated using dry film resist", Optics Express, vol. No. 15, No. 19, pp. 12088, Jan. 1, 2007.

Tzu-Chien et al., "Fast fabrication of integrated surface-relief and particle-diffusing plastic diffuser by use of a hybrid extrusion roller embossing process", Optics Express, vol. No. 16, No. 1, pp. 440, Jan. 1, 2008.

Velten et al., "Investigations on reel-to-reel hot embossing", The International Journal of Advanced Manufacturing Technology, vol. No. 47, No. 1-4, pp. 73-80, Feb. 24, 2009.

Yeo et al., "Micro-fabrication of polymeric devices using hot roller embossing", Microelectronic Engineering, vol. No. 86, No. 4-6, pp. 933-936, Apr. 1, 2009.

Maximilian et al., "Lab-on-a- Foil: microfluidics on thin and flexible films", Lab on a Chip, vol. No. 10, No. 11, pp. 1365, Jan. 1, 2010.

Stefanie et al., "Thermoresponsive PEG-Based Polymer Layers: Surface Characterization with AFM Force Measurements", vol. No. 26, No. 5, pp. 3462-3467, Mar. 2, 2010.

Velten et al., "Roll-to-Roll Hot Embossing of Microstructures", Design Test Integration and Packaging of MEMS/MOEMS (DTI P), pp. 326-331, 2010 Symposium on, May 7, 2010.

Anonymous, "Melinex 454", Fly-supply.com, XP002672166, Retrieved from the Internet: URL:http://www.fly-supply.com/Melinex-Films/Melinex-454/Detailed-product-flyer.html [retrieved on Mar. 22, 2012].

Korin et al., "Design of Well and Groove Microchannel Bioreactors for Cell Culture", Biotechnology and Bioengineering, vol. No. 102, Issue No. 4, pp. 1222-1230, May 1, 2009.

Lindstrom et al., "High-Density Microwell Chip for Culture and Analysis of Stem Cells", PLoS ONE, vol. No. 4, Issue No. 9, pp. 1-9, Sep. 30, 2009.

Chinese Office Action issued in connection with corresponding CN Application No. 201180060701.9 on May 6, 2014.

McMurray et al.,"Nanoscale surfaces for the long-term maintenance of mesenchymal stem cell phenotype and multipotency", Nature Materials, Aug. 2011, vol. 10, 8 Pages.

Manbachi et al. "Microcirculation within Grooved substrates regulates Cell positioning and Cell Docking inside Microfluidic Channels", Lab Chip, pp. 747-754, May 2008.

BD Biosciences, BD Biocoat—Dish 35MM PLL 5PAC 20CAS, 2010.

CNMC, dosimetry phantoms, p. 1, accessed Aug. 3, 2015.

Collignon et al., "Integrity™ Xpansion™ Multiplate Bioreactor: The Scalable Solution for Adherent Stem Cell Expansion", ATMI LifeSciences, 2010.

Funakoshi General Catalog 2005-2006 devices edition, pp. viii-ix, Dec. 22, 2005.

Moeller et al. "A microwell Array system for stem cell culture", pp. 752-763, Nov. 14, 2007.

Khorasani et al., "Plasma Surface Modification of Poly (I-Lactic acid) and Poly (lactic-co-glycolic acid) Films for Improvement of Nerve Cells Adhesion", Radiation Physics and Chemistry, pp. 280-287, vol. No. 77, Issue No. 3, Mar. 2008.

Kohen et al., "Characterization of Matrigel interfaces during Defined Human Embryonic Stem Cell Culture", Biointerphases, pp. 69-79, vol. No. 4, Issue No. 4, Dec. 2009.

Lee et al., "Response of human chondrocytes on polymer surfaces with different micropore sizes for tissue-engineered cartilage", J Appl Polym Sci., vol. No. 92, pp. 2784-2790, 2004.

Khabiry et al.; "Cell Docking in Double Grooves in a Microfluidic channel", 9 Pages, 2009.

Satoh et al, "Cultivation of Human Induced Pluripotent Stem Cells with Controlled Aggregate Size and Geometrical Arrangement by Inverting Microwell Array Chip", 17th International Conference on Miniaturized Systems for Chemistry and Life Sciences, pp. 1701-1703, Issue No. 27-31, Oct. 2013.

Thormann et al., "Interactions between a Polystyrene Particle and Hydrophilic and Hydrophobic Surfaces in Aqueous Solutions", Langmuir, vol. No. 24, Issue No. 14, pp. 7278-7284, 2008.

Ueda et al., "Substrates for Human Pluripotent Stem Cell Cultures in Conditioned Medium of Mesenchymal Stem Cells", Journal of Biomaterials Science, Polymer Edition, pp. 153-165, vol. No. 23, Issue No. 1-4, Apr. 13, 2012.

Van-Kooten et al., "Plasma-treated polystyrene surface: model surfaces for studying cell-biomaterial interactions", Biomaterials; vol. No. 25, pp. 1735-1747, 2004.

Wave Bioreactor Catalog2006, Wave Europe, pp. 1-13, 2006.

International Search Report and Written Opinion issued in connection with PCT Application No. PCT/EP2011/073064 on May 9, 2012.

Unofficial English translation of Office Action issued in connection with corresponding CN Application No. 2011800607019 on Jul. 6, 2015.

Unofficial English translation of Office Action issued in connection with corresponding JP Application No. 2013543815 on Dec. 15, 2015.

* cited by examiner

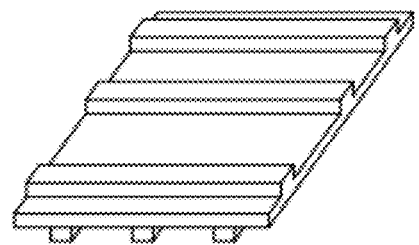
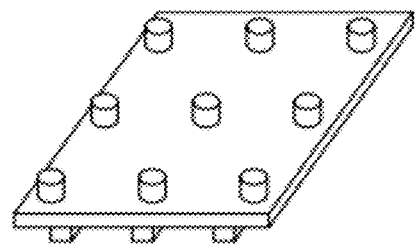
FIG. 2A  FIG. 2B
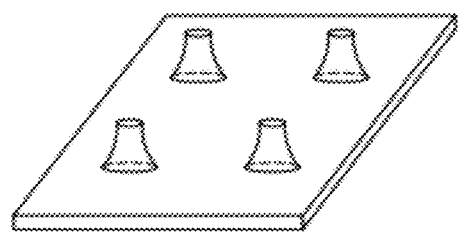
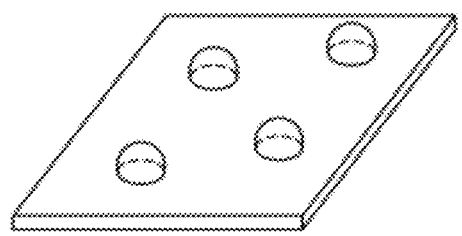
FIG. 2C  FIG. 2D

CELL CARRIER, METHODS OF MAKING AND USE

CROSS REFERENCE TO RELATED APPLICATIONS

This application is a continuation-in-part of U.S. patent application Ser. No. 12/970,735, entitled "Cell carrier, associated methods for making cell carrier and culturing cells using the same", filed Dec. 16, 2010; which is herein incorporated by reference.

FIELD

The invention relates to cell carriers, and associated methods for making and using the cell carriers. More particularly, the invention relates to polymer based cell carriers for cell growth.

BACKGROUND

Adherent cells have conventionally been grown on glass surfaces or on polymer substrates. Surfaces for cell culture are often pre-treated to enhance cell adhesion and proliferation. A wide variety of static culture vessels is available for adherent cell culture in the laboratory. While static culture vessels such as tissue culture flask or multi-layer cell growth flasks do allow for some scale-up of adherent cell culture, they become limiting at larger scales as they are labor-intensive, subject to variability due to manual processing, and limited in volumetric productivity (e.g. cell yield per volume of incubator space).

Cell culture using bioreactors has long been practiced as the preferred scale-up method for cell culture. The use of microcarriers for adherent cell culture is common in industrial practice, such as in bioprocessing. Microcarrier beads, or planar carriers have been developed to provide increased surface area for cell attachment, and to enable high-density adherent cell culture on an industrial scale.

Typical bioreactor vessels employ some means of agitation, such as internal impellers, rocking or shaking mechanisms to suspend the cells and allow mass transfer of nutrients, oxygen and metabolic waste products. Conventional carriers can be prone to sticking to the walls of reactors and other surfaces; also, planar carriers can be prone to stacking/clumping as cell growth proceeds, particularly when the agitation in the bioreactor is intermittent rather than continuous. This can affect cell growth and nutrient/metabolite transport as well as cell release.

Therefore, there is a need for a carrier for adherent cell growth that avoids clumping of carriers to each other or sticking of carriers to the wall/other surfaces of the reactor, so that it facilitates uninterrupted cell expansion, visualization, and release. Efficient cell expansion is particularly important for high yield industrial scale cell culture processes for adherent cells, including such shear-sensitive cells as mesenchymal stromal cells (MSCs), which are currently expanded in static culture vessels. Therefore, the development of cell culture carriers that facilitate cell attachment, proliferation and release, and that reduce stacking and sticking of the carriers is highly desirable.

BRIEF DESCRIPTION

The invention relates to carriers for cell culture and methods of making and using the carriers. One or more embodiments of the carrier for cell culture comprise one or more relief features.

One example of a method of culturing adherent cells, comprises providing a carrier for growing the cells, comprising one or more surfaces; and one or more relief features on one or more of the surfaces, wherein the carrier has a length at least about 0.2 mm, a width at least about 0.2 mm, and a height in a range from about 0.012 mm to 0.5 mm; and wherein each of the relief features/indentations has a height above the surfaces in a range from about 2 to 200 µm, and width in a range from about 20 to 200 µm; seeding the cells on the carriers; and growing the cells on the carrier.

Another example of a method of culturing adherent cells, comprises providing a carrier for growing the cells, comprising one or more surfaces; and one or more relief features on one or more of the surfaces, wherein the carrier has a length at least about 0.2 mm, a width at least about 0.2 mm, and a height in a range from about 0.012 mm to 0.5 mm; and wherein each of the relief features/indentations has a height above the surfaces in a range from about 2 to 200 µm, and width in a range from about 20 to 200 µm; seeding the cells on the carriers; loading the carriers to a disposable housing comprising fluid; loading the disposable housing to a bioreactor; and growing the cells on the carrier in the bioreactor.

In another example, a method for culturing cells, comprises providing carriers for growing the cells, comprising one or more surfaces; and one or more relief features on one or more of the surfaces, wherein the carrier has a length at least about 0.2 mm, a width at least about 0.2 mm, and a height in a range from about 0.012 mm to 0.5 mm; and wherein each of the relief features/indentations has a height above the surfaces in a range from about 2 to 200 µm, and width in a range from about 20 to 200 µm; seeding the cells to a disposable housing pre-loaded with the carriers; attaching the cells to the carriers with an agitation cycle; and growing the cells on the carrier in the same agitation cycle or a different agitation cycle.

DRAWINGS

These and other features, aspects, and advantages of the present invention will become better understood when the following detailed description is read with reference to the accompanying drawings in which like characters represent like parts throughout the drawings, wherein:

FIG. 2 is an example of series of images of carriers of the invention comprising one or more relief features with design of (A) ridges (B) cylindrical posts (C) profiled posts and (D) domed protrusions on one or both sides of the base.

FIG. 4 is an example of series of images of carriers of the invention comprising one or more relief features with design of: (A) ridges (Prototype 1) (B) cylindrical posts (Prototype 2), domed protrusions using (C) hollow glass spheres embedded in polystyrene film (Prototype 3) (D) solid glass spheres embedded in polystyrene film (Prototype 4) and (E) polystyrene beads embedded in polystyrene film (Prototype 5).

Figure 5:
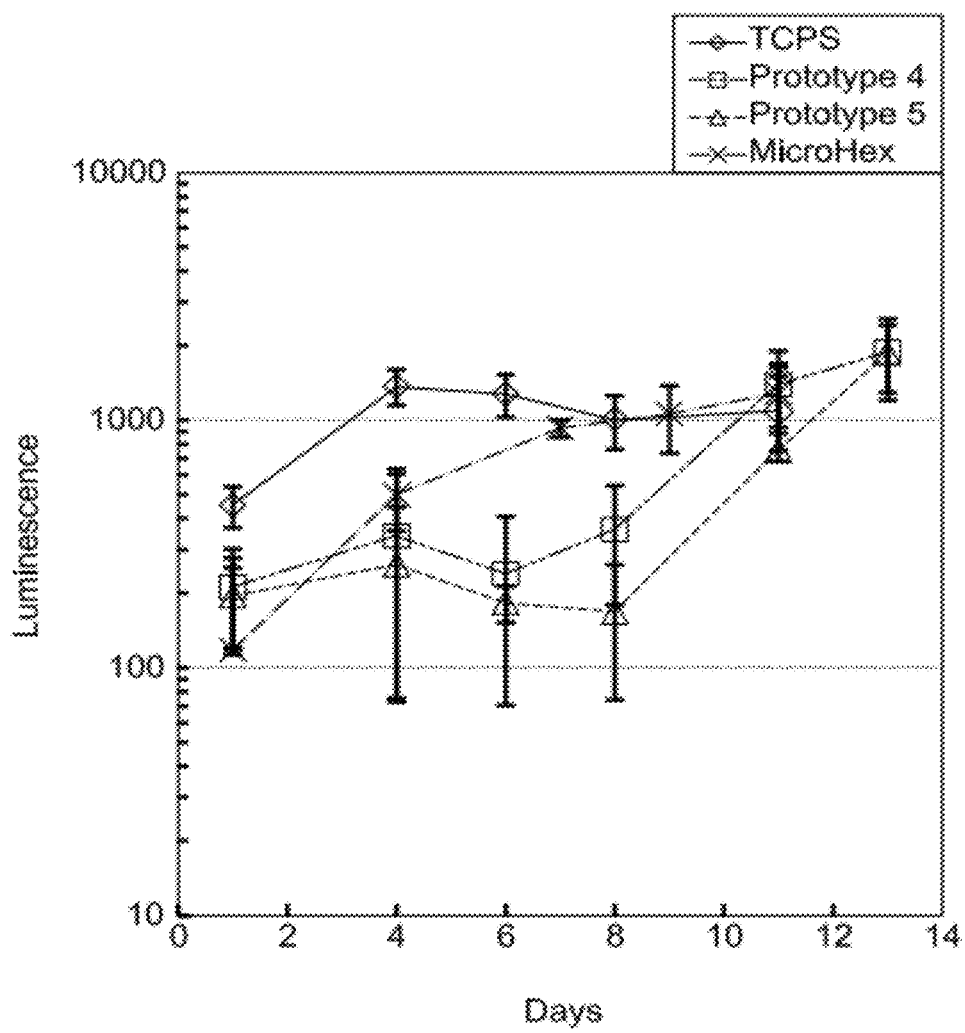

FIG. 5 is an example of graph showing growth of human mesenchymal stromal cells (hMSCs) cultured in STR using carriers with relief features of different designs, carriers flat hexagonal structure (such as MicroHex™), and hMSCs cultured on flat tissue culture polystyrene surface (TCPS) in static culture medium.

Figure 6A:
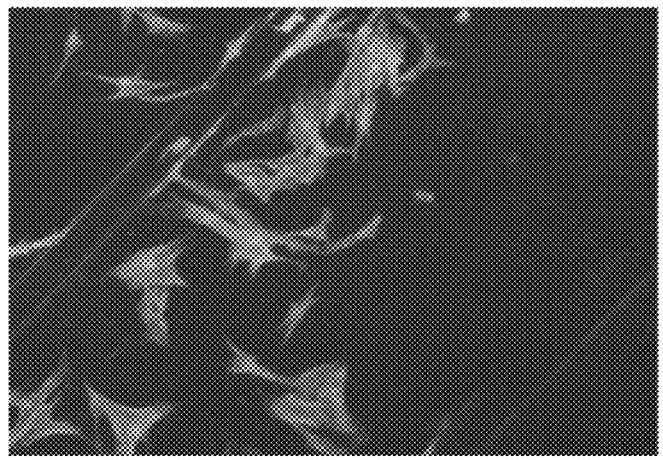
Figure 6B:
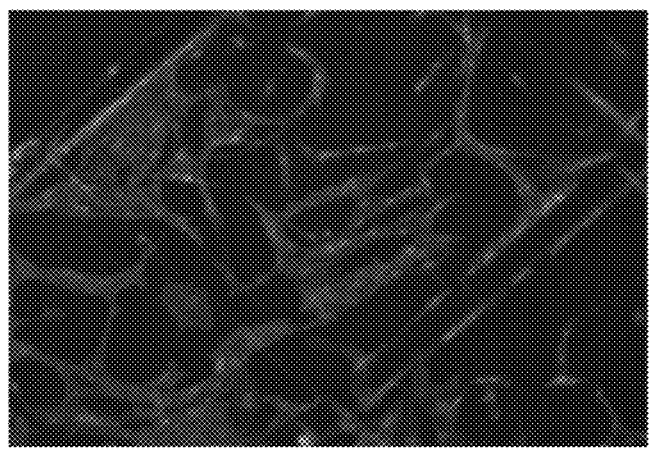
Figure 6C:
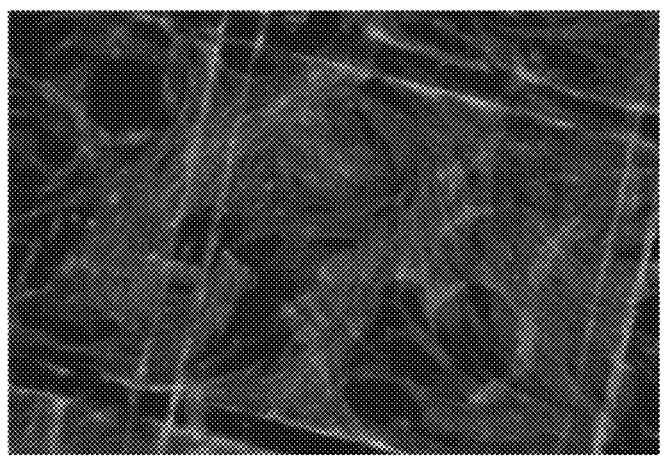

FIG. 6 is an example of series of 100× optical microscopy images of hMSCs grown on the carrier of the invention, illustrating cell growth on top of the carrier surface with ridge-like relief features at (A) day 1, (B) day 5, and (C) day 7.

Figure 7A:
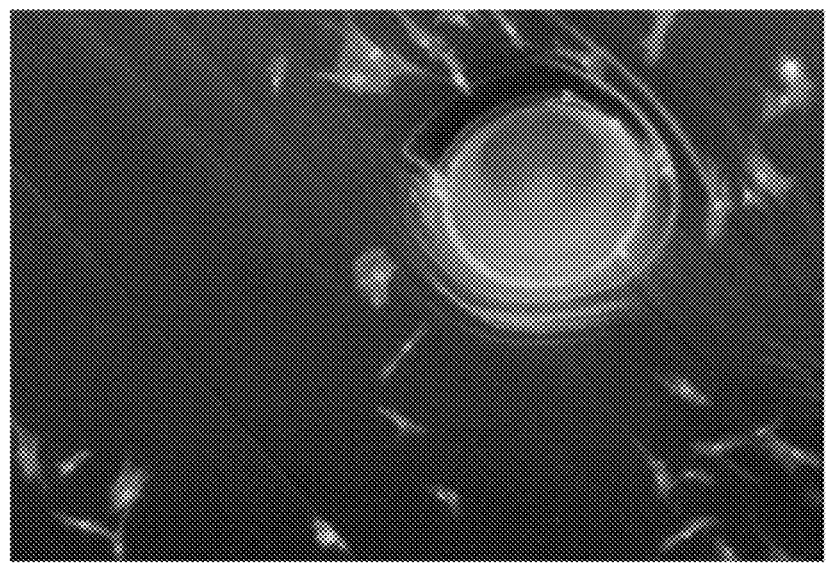
Figure 7B:
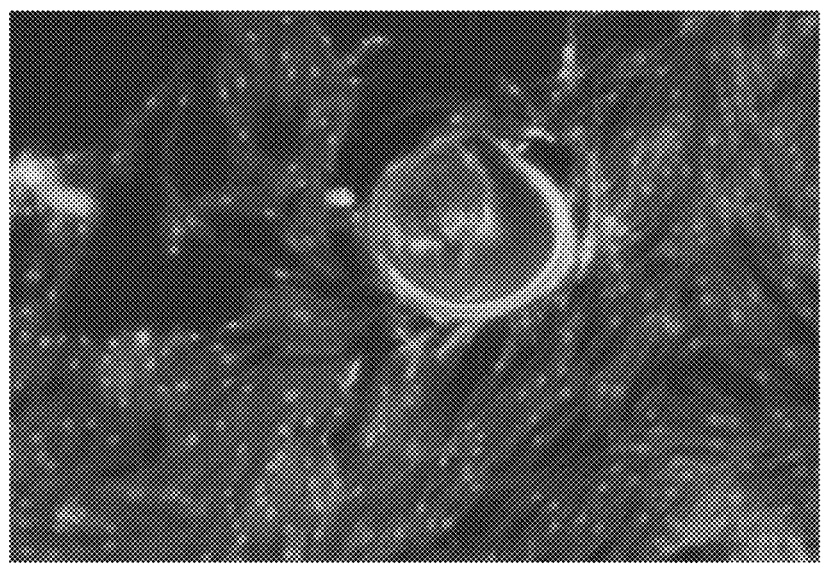

FIG. 7 is an example of series of 100× optical microscopy images of hMSCs grown on the carrier of the invention, illustrating cell growth on the carrier fabricated with polystyrene beads to provide relief features at (A) day 1, and (B) day 6.

Figure 8A:
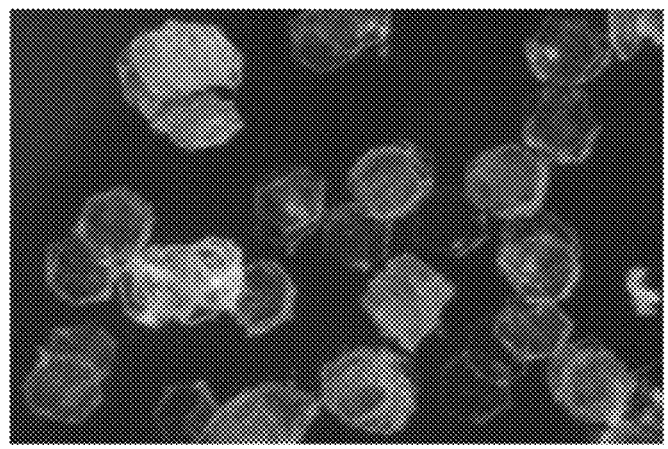

FIG. 8 is an example of series of 100× optical microscopy images of hMSCs grown on the carrier of the invention, illustrating (A) clumping of MicroHex™ carriers after 7 days of culture, no physical connection for (B) carriers with relief features of parallel ridges after 7 days of culture and (C) carriers with relief features of polystyrene beads after 6 days of culture.

Figure 9:
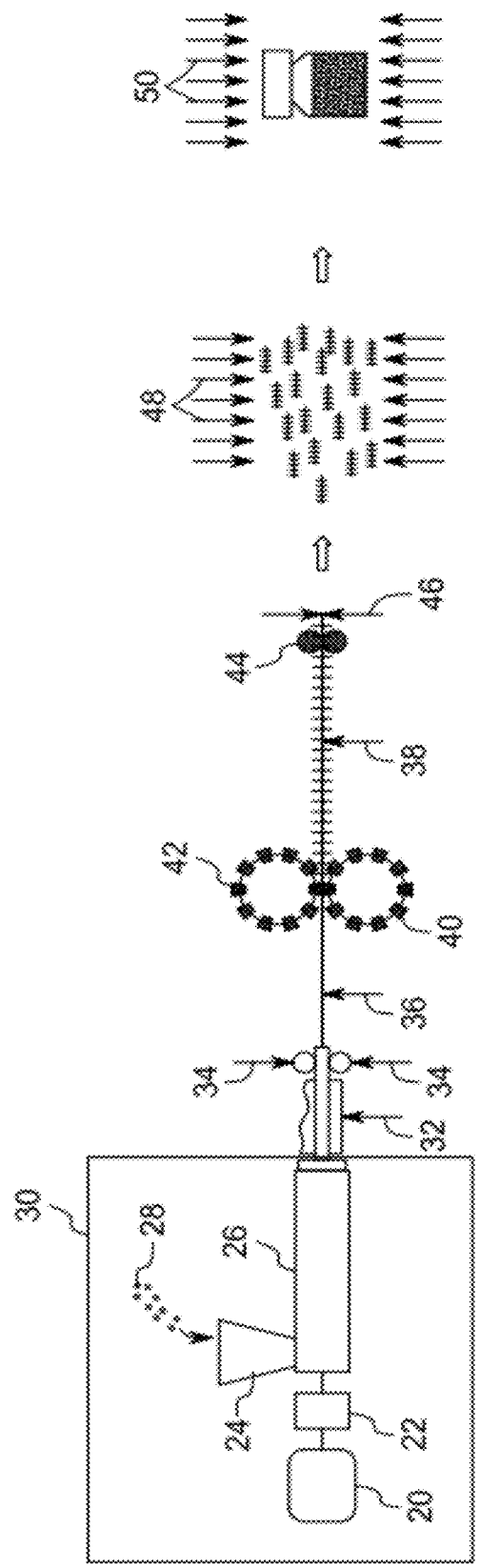

FIG. 9 is a schematic drawing of an example of a process of manufacturing carrier using roll-to-roll embossing process.

Figure 10A:
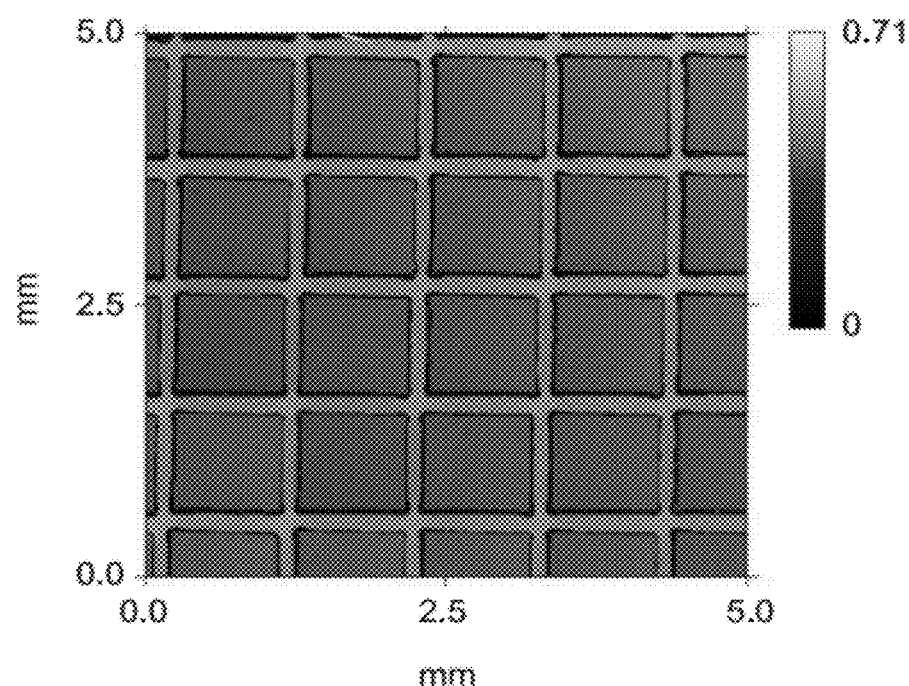
Figure 10B:
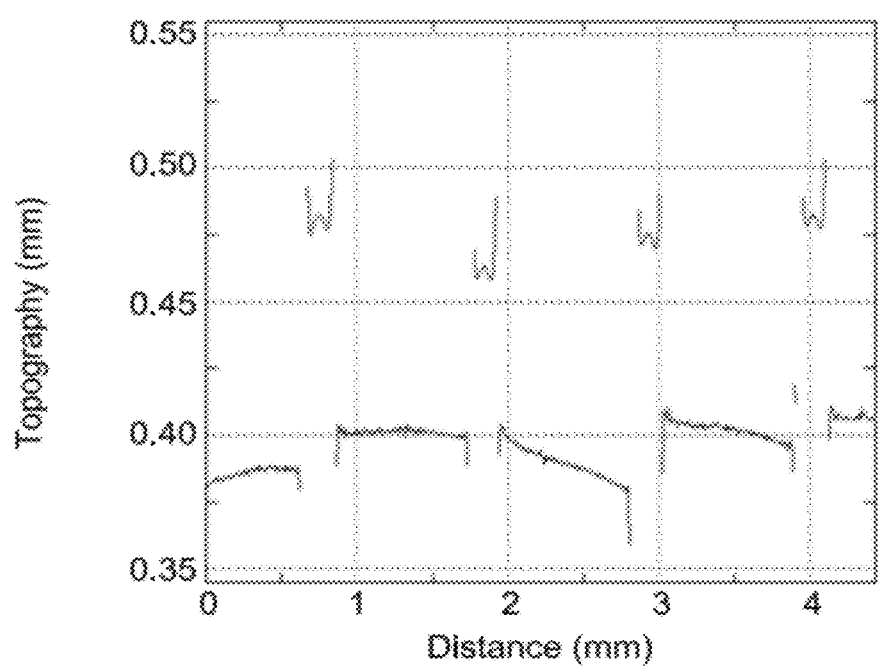

FIG. 10 A is an example of an embossed carrier using continuous roll-to-roll type embossing process, and FIG. 10 B shows the topography of embossed waffle pattern by chromatic white light profilometry.

DETAILED DESCRIPTION

One or more of the embodiments of the invention relate to a carrier for growing adherent cells, wherein the carrier is suspended in a bioreactor wherein the carrier is useful for efficient cell adhesion, cell growth, and cell release. High yield of cells is required in various applications involving cell culture, and this carrier may meet that requirement.

To more clearly and concisely describe the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

As used herein, the term "carrier" or "carrier for growing cells" refers to a support for adhering and culturing cells. The carrier has relief features on it. Suitable materials of the carrier may include, but are not limited to, polymers, copolymers or blends of polymers. The carrier may further be coated with a suitable coating material for effective cell adherence, proliferation and functionality.

As used herein, the term "relief feature", refers to a pattern or feature on a carrier surface, which helps to reduce adherence of highly adherent cells grown on surfaces of the different cell carriers. Therefore, the adherent cells which are attached to a carrier surface may not further attach to a surface of another carrier or inner walls of the bioreactor. In this example, the tendency of the carriers to stack and stick to each other by bridging of the cells from one carrier to another is reduced due to presence of this patterned surface or relief features on the surface. These relief features minimize stacking of the carriers, reducing interaction with each other and sticking of the carriers to the inner walls of the reactor.

Embodiments of the carrier in suspension comprise one or more outer surfaces; wherein one or more of the outer surfaces of the carrier comprise one or more relief features. The invention also comprises methods of making the carrier, and methods and kits for culturing cells using the carriers for cell growth.

Figure 1:
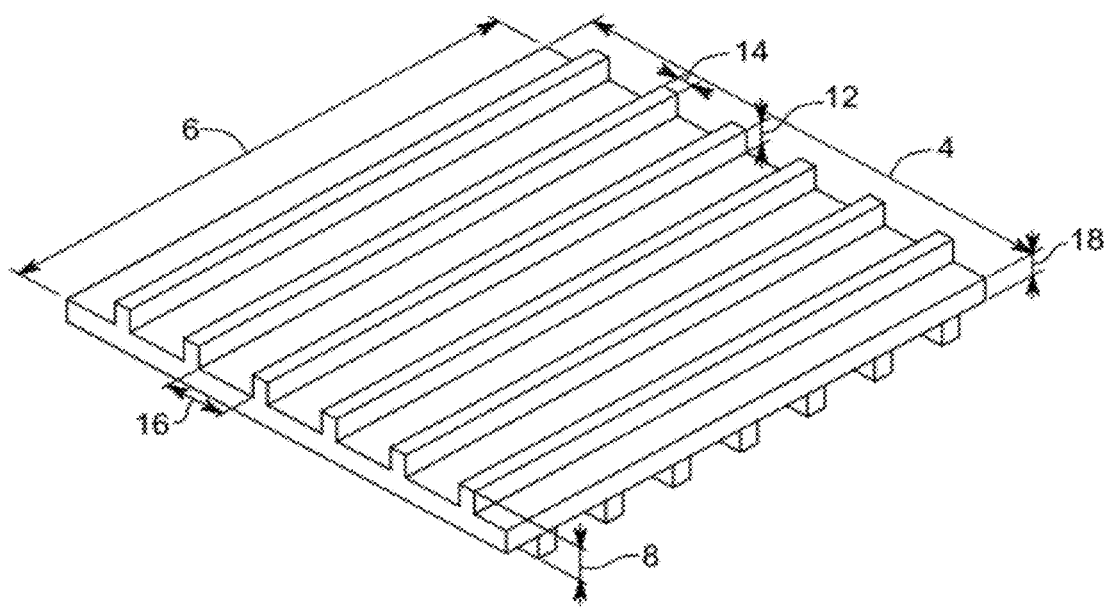
FIG. 1 is an example of image of a carrier of the invention comprising a plurality of relief features showing dimensions of the carrier and each relief feature.

The carrier for growing adherent cells, comprises one or more outer surfaces; and one or more relief features are present on one or more of the surfaces, wherein an example of the carrier is shown in FIG. 1. In one or more examples, the carrier has a length at least about 0.2 mm, a width of at least about 0.2 mm, and a height in a range from about 0.012 mm to 0.5 mm. In some embodiments, the carrier has a length in a range from about 0.2 mm to 5 mm, a width in a range from about 0.2 mm to 5 mm, and a height in a range from about 0.012 mm to 0.5 mm. One or more relief features are designed on the carrier surface, for example, as shown in FIG. 1. The relief feature comprises a height and a width, wherein the height is in a range from about 2 to 200 µm, and width is in a range from about 20 to 200 µm. In one or more embodiments, a distance between every two relief features is in a range of about 50 to 1000 µm.

In one example of carrier 2 as shown in FIG. 1, has a length 4, width 6, and height 8. As noted, the carrier 2 has a length 4 at least about 0.2 mm, a width 6 at least about 0.2 mm, and a height 8 in a range from about 0.012 mm to 0.5 mm. In some embodiments, the carrier has a length 4 in a range from about 0.2 mm to 5 mm, a width 6 in a range from about 0.2 mm to 5 mm, and a height 8 in a range from about 0.012 mm to 0.5 mm. In some embodiments, the carrier has a length 4 in a range from about 0.2 to 2.5 mm and width from about 0.2 to 2.5 mm. A distance 16 between every two relief features is in a range of about 50 to 1000 µm.

Highly adherent cells have a tendency to adhere on the surface. Therefore, the adherent cells which are attached to a carrier surface may have further affinity to attach to a surface of another carrier or inner walls of the bioreactor and that enhance the stacking or sticking process. In this example, the tendency of the carriers to stack and stick is exacerbated by bridging of the cells from one carrier to another, and forming linkages between two or more carriers. To minimize stacking of the carriers, reducing interaction with each other and sticking of the carriers to the inner walls of the reactor, one or more relief features are designed on the carrier surface. As noted, embodiments of the relief features as shown in FIG. 1 comprise a height 12, a width 14 and thickness 18, wherein the height 12 is in a range from about 2 to 200 µm, the width 14 is in a range from about 20 to 200 µm and the thickness 18 is about 10 to 75 µm. As shown in FIG. 1, the total height 8 includes the height 12 of the relief features, and membrane thickness 18 of the carrier. In case of carriers having relief features on two opposite surfaces, as shown in FIG. 1, height 8 includes the height 12 of each of the relief features (2× height 12), and thickness of the carrier. For example, if the relief features present on both side of the carriers has same height 0.002 mm and membrane thickness 0.011 mm, then total height 8 of the carrier is (2×0.002+0.011)=0.015 mm.

The relief features may have variety of structures, shapes and sizes. Examples include but are not limited to, a ridge, a post, a domed protrusion, a bead or a combination thereof. Post structures may include but are not limited to cylindrical posts or profiled posts. Beads may include, but are not limited to, elliptical or spherical shapes. In some embodiments, the relief feature may be present on both opposing surfaces of the carrier. When both surfaces of the carrier have relief features, it increases the effectiveness in preventing carrier stacking and sticking.

The ridges may be present on the carrier surface with an angle, wherein the angle may be in a range of, greater than 0 degree and less than 180 degree. In one embodiment, the ridge-like structures may be perpendicular to the carrier surface, as shown in FIGS. 1, and 2 (A). In one example, the width of the ridges 14 may be in a range of 20 to 75 µm, height 12 may be in a range of about 20 to 50 µm. In some embodiments, the design of the ridge is different, and the ridge may look like a series of raised pins projecting from the surface, which are perpendicular to the plane of the carrier.

A "post" structure of relief feature as shown in FIG. 2 (B) may be a structure that resembles with a raised pin from the surface of the carrier. "Post" like structures may have a diameter in a range of about 25 to 200 µm, a height in a range of about 20 to 200 µm, and a distance between the posts are in a range of 50 to 500 µm. In one or more embodiments, the relief feature is a "profiled post" structure, as shown in FIG. 2 (C). In some other embodiments, the relief feature is a "spherical or domed protrusion", as shown in FIG. 2 (D).

Figure 3A:
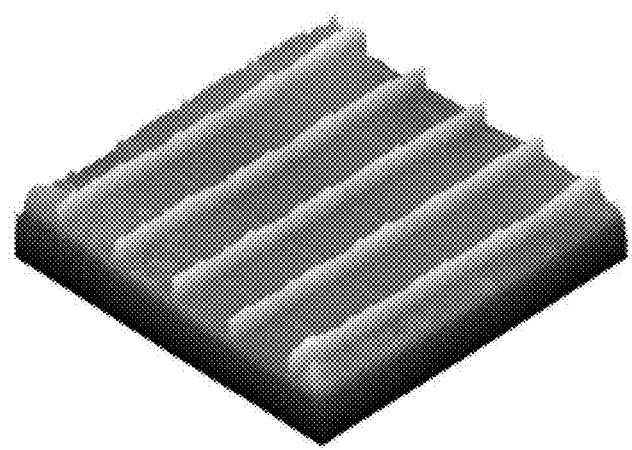
FIG. 3A is an example of a carrier design with ridge-like relief feature.
Figure 3B:
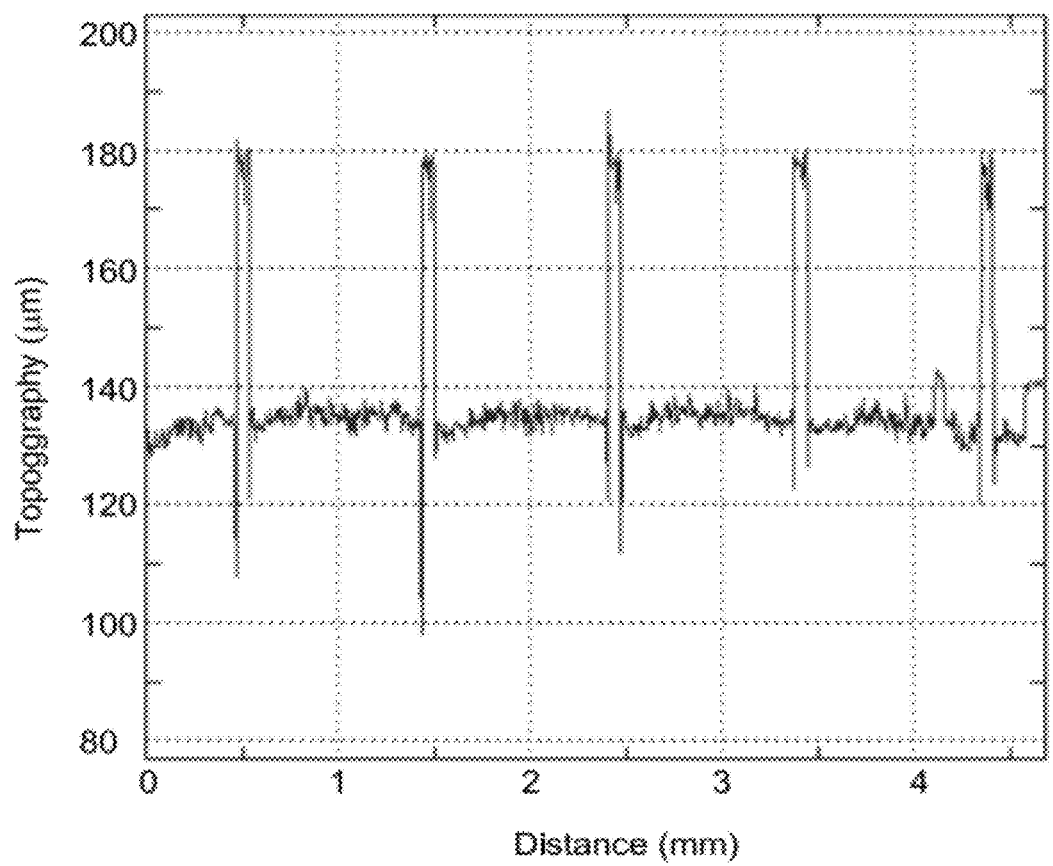
FIG. 3B is an example of topography by chromatic white light profilometry showing homogeneity in distance between each of the ridges present on a surface of a carrier.
Figure 4A:
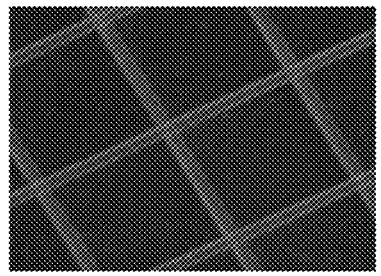
Figure 4B:
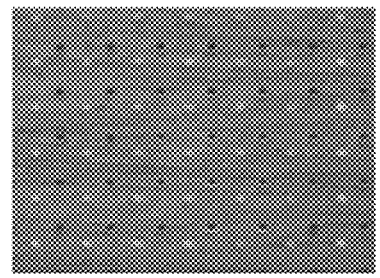
Figure 4C:
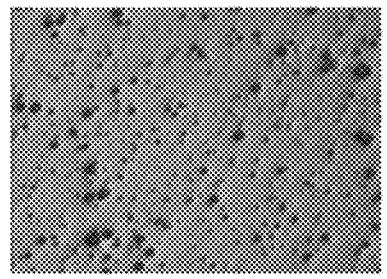
Figure 4D:
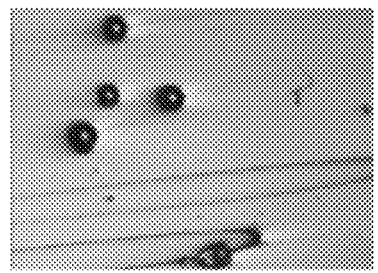
Figure 4E:
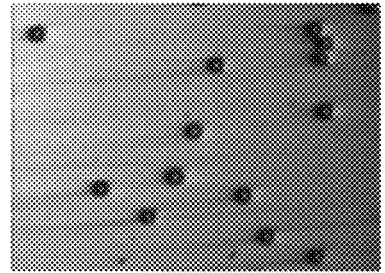

As noted, in some embodiments, the carriers are fabricated with relief features with parallel ridges, wherein the distance between each of the ridges may be uniform as shown in FIG. 3 (A). The uniformity in distance between each of the ridges is represented by a topography via chromatic white light profilometry with a change in distance, as shown in FIG. 3 (B). For example, the distance 16 between two of the ridges is about 1000 µm, as shown in FIG. 1 and FIG. 3 (B). In one example, for post-like relief features, the distance between two posts is about 500 µm. In some embodiments, the carriers are fabricated with relief features of a series of parallel ridges which are perpendicular to the surface, and post, and the optical microscope images of ridge and post are shown in FIGS. 4 (A), and (B) respectively. The image of FIG. 4(A) shows parallel ridges (each of the ridges is parallel to other) at top and bottom surfaces. In this case, while the ridges are perpendicular to one surface, and the ridges are perpendicular to the other surface, the arrangement to both sides of the carrier provides equal stiffness in vertical and horizontal directions.

As noted, in some embodiments, the relief features are spherical protrusions from the surface; in some cases, a hemisphere or a part of a spherical bead may protrude from the surface. In one example, the features are made of spherical beads which are embedded in the film and partially deform the film surface. The spherical beads may be formed, for example, of glass, polymer, ceramic or metal. In one embodiment, "beads" may be small glass spheres, which are embedded in the polystyrene film. The diameter of the spherical beads may be in a range from about 20 to 200 µm. In one example, the diameter of the spherical bead is about 45 µm. In one example, the glass spheres are hollow glass spheres, which are embedded in the polystyrene film to force the film surface to conform over the sphere and make a dome-like structure on the film surface. The hollow glass spheres as shown in FIG. 4 (C), in some example, have a diameter of about 45 µm. In another embodiment, the beads are solid glass spheres, which are embedded in the polystyrene film, as shown in FIG. 4 (D). The diameter of the solid spherical glass beads is in a range from about 20 to 200 µm. In one example, the solid glass spheres are disposed on the polystyrene film, which has diameter of about 180 µm as shown in FIG. 4 (D). In another example, the polystyrene beads, which are embedded in the polystyrene film is shown in FIG. 4 (E), wherein the beads have diameter of about 200 µm. In some examples, the relief feature is constructed on the carrier surface using polystyrene beads. The beads are embedded in the film to distort the surface of the carrier and form relief features. The height of the protrusion or relief feature depends on the size of the beads. The bead-size may be customized based on the characteristics of various cells, such as adherent behavior of the cells.

A cross sectional profile of each relief feature may have, as non-limiting examples, a polygonal, circular arc, or elliptical arc shape. Each of the polygonal relief features may have, as non-limiting examples, a triangular, rectangular, square, trapezoidal, pentagonal or hexagonal shape. The dimension of the diameter, length and width of the relief features may be the same or different.

The relief feature, which protrudes from the surface of the carrier, should have a height sufficient to allow easy liquid flow through the carrier or between the surface of a carrier and the wall of a culture vessel, e.g. bioreactor, which may promote oxygen and nutrients transfer and metabolic byproduct removal especially at static condition. However, the feature should not be so high that it causes substantial reduction in packing density of carriers per unit volume, which correlates to the cell yield per reactor volume. The desired range of "projection" of the feature above the plane of the carrier is optimized at about 2 microns to about 200 microns, and more specifically from 2 microns to about 50 microns. The relief features are designed to be robust enough to survive dense large scale culturing processes.

In some embodiments, the carrier has a substantially planar disc-like structure with relief features on the planar surface. As used herein, 'substantially planar disc', refers to a disc, which provides 85-90% planar surface area for growing cells. The shape of the carrier may be polygonal. In one or more embodiments, the shape of the carrier may vary, for non-limiting examples, the carrier may have an overall perimeter that is circular, elliptical, triangular, rectangular, square, pentagonal, or hexagonal shape.

The disc like-structure of the carrier may provide higher surface area per unit volume for culturing cells, relative to other structures, e.g. spherical structures. Efficient separation of released (e.g. enzymatic release) cells from the carriers is facilitated due to the significant size difference between the cells (~15 micron) and the carriers (larger than 0.2 mm). Released cells may be separated from the carriers via simple filtration, or separation of the supernatant after allowing the carriers to settle. The presence of relief features allows fluid flow between the carriers even once the carriers settle into the reactor, further facilitating cell/carrier separation, whereas flat carriers and spherical carriers tend to form a clump that resists fluid flow and cell/carrier separation.

The carriers are used in suspension inside a bioreactor, comprising a fluid having a convective motion that generates sufficient transport of nutrients and oxygen to the cells. The cells adhere to the surface of the carrier comprising the relief features, wherein in one embodiment, the carrier has a flat or curved wall of sufficient height such that the effect of fluid-induced hydrodynamic stress on the cells is minimized. In some embodiments, the carrier has one or more surfaces, and one or more walls surround those surfaces. An example of a cylindrical carrier is a cup shaped carrier. In one embodiment, the carrier may have a continuous wall surrounding the both side of the base of the carrier. In one example, two walls may separately surround the top and bottom of the base, as in, one cup is present on the top of the base and another cup is present on the bottom of the base. The walls of each of the cup shaped carriers may have different heights or thicknesses. In one embodiment, the surface or base of the carrier may have one or more indentations, which results in a multiple pockets on the carrier surface.

In some embodiments, the carrier comprises an optimum height of the relief features, balancing the needs of the cells to access nutrients and remove/dilute metabolites, while culturing cells and avoiding carrier stacking and sticking. The relief features on the carrier serve in part to prevent the carriers from sticking to the inner walls of the reactor or culture vessel, which in part facilitates cleaning the reactors/culture vessels between batches of cell culture in case of non-disposable reactor. The cleaning of the culture vessels between two or more batches of cell culture becomes easier when the carrier sticking is reduced. The carriers may have particular utility in large-scale applications such as bioprocessing, where the currently used reactors have stainless steel or glass inner surfaces. In this case, reduction of carrier sticking to the walls of the reactor is desirable.

The carrier may be made of glass, polymer, ceramic, metal or a combination thereof. In one embodiment, the carrier is made of a polymer or a copolymer or a blend of polymers. The polymers may comprise, but are not limited to synthetic and natural polymers such as, polyester including polyethylene terephthalate (PET), polystyrene, polycarbonate, polyamide, polyurethane, olefin polymers, dextran, silicone, or polyacrylate, or copolymer or blend of polymers thereof. In one embodiment, the carrier is made of polystyrene. The density of the material used for carrier determines the suspension behavior of the carrier in the liquid media. In one example, the polystyrene based carrier has a density of 1.04 g/mL, which is close to the density of water/media (density=1), resulting in better suspension in the liquid.

The carrier may be transparent, which allows cell observation under an optical microscope. In certain embodiments, the carrier has a substantially planar disc shape, which facilitates cell visualization by preventing lensing effects. Refraction of light can be a hindrance to visualization of cells on spherical carriers of certain refractive index. Cell visualization is useful, for example, for culturing and monitoring cells during vaccine production or stem cell expansion. In some embodiments, the polymer and surface treatment is substantially free of components of animal origin. This is especially beneficial in therapeutic applications, e.g. in the production of cells for cellular therapies. The polymer may be rigid at room temperature/cell culture temperature, non-porous and may have non-swelling properties in water, phosphate buffered saline (PBS) or growth medium. The rigid, non-swelling, non-porous properties of the polymer can facilitate cell release, for example, when using standard trypsinization protocols.

To maintain sterility of the cell culture system, the carriers should be sterilized before use for culturing cells. In one or more embodiments, the carriers may be sterilized using autoclaving or gamma-sterilization. In one example, the polystyrene based carrier is gamma sterilizable. The carriers provide a balance of ease of sterilization, high surface area or volume, ability to visualize cells easily and ability to release cells easily, while avoiding stacking of the multiple carriers and sticking of the carriers to the surface of the reactor.

The polymer-based carrier surfaces are optionally modified with functional groups or coatings to enable better cell attachment and growth. In some embodiments, a surface treatment is imparted to the patterned polymer film comprising one or more of corona discharge treatment, gas plasma treatment, chemical functionalization or coating. A variety of biomolecules may also be used to modify surfaces of the carriers to enhance cell attachment. Non-limiting examples of the biomolecules include collagen, fibronectin, vitronectin and laminin. In one embodiment, the surfaces are modified with recombinant fibronectin to enhance surface cytophilicity for better attachment of the cells. The surface modification may result in a change, for example, in hydrophobicity or hydrophilicity. Increased hydrophilicity additionally benefits the carrier by promoting wetting of the carrier by water, and preventing it from being trapped at the air-interface by surface tension forces.

In some embodiments, the surfaces are treated with corona discharge to modify one or more surface properties of the carriers. In corona discharge treatment, a current develops from an electrode with a high potential in a neutral gas, such as air. Ionization of the gas generates a layer of plasma around the electrode. The ions generated eventually pass the charge to nearby areas of lower potential, or recombine to form neutral gas molecules. Surfaces of organic films such as polystyrene, polyesters and others may be oxidized when exposed for a short time to the reactive air plasma by corona discharge surface treatment. Corona discharge treatment can increase the oxygen content on the polymer surface and improve the film wettability by water.

The surface modification may alternatively be achieved via plasma treatment. In some embodiments, the surface is treated with plasma to modify the surface properties of the carrier. Plasma treatment is carried out in a plasma reactor, which is a vacuum vessel with a gas at low pressure, typically 10 to 1000 mTorr. When a high frequency electric field is generated in the reactor, a plasma is formed containing reactive species like ions, free radicals and vacuum-UV photons. These species react with the polymer surface and cause a chemical modification with various properties depending on the nature of the gas and the plasma parameters. Gases such as oxygen, ammonia and argon are typically used for chemical modification of the surfaces and cell-adhesion improvement on polymer surfaces. In one embodiment, the polymer surface is modified by oxygen-plasma treatment to increase the cytophilicity of the surface. The surface functionality may also be altered via wet chemical methods such as oxidation treatments using perchloric acid or permanganate or partial hydrolysis using strong acids or bases.

A coating may also be applied on each of the surfaces to change the surface chemistry and physical properties of the carriers, e.g. chemical functionality, biochemical functionality, hydrophobicity, hydrophilicity, or wettability. One index of hydrophobicity/hydrophilicity is contact angle of a water droplet on the surface. Contact angle can be measured by techniques well-known in the art. The water contact angle for the coated carrier surface may be in a range from about 10° to about 90°, or in some embodiments the water contact angle is from 30° to 70°. The carrier surface may be modified, for example, to enhance cell release as well as cell attachment. The coating may be made, for example, of a thermoresponsive polymer, pH responsive polymer, or combination thereof. Thermoresponsive polymers may include, but are not limited to, poly(N-isopropylacrylamide) (PNIPAM), poly(di(ethyleneglycol)methylether methacrylate) (PDEGMA). pH responsive polymers may include, but are not limited to, copolymers of acrylic acid, dimethylaminoethylacrylate, and hydroxyethylacrylate. The coating may comprise one or more layers. In some embodiments, where the coating comprises multiple layers, the layers may be homogeneous or heterogeneous. For one example, one layer may be made of thermoresponsive polymer, and another layer may be made of pH responsive polymer. Thermoresponsive or pH responsive polymer coatings on the surface can facilitate non-enzymatic release of cultured cells from the carrier surface.

A cell culture kit comprises one or more of the carriers, wherein the carrier comprises one or more surfaces; and one or more relief features are present on one or more of the surfaces. Each of the carriers present in the kit, has a length at least about 0.2 mm, a width at least about 0.2 mm, and a height in a range from about 0.012 mm to 0.5 mm; and wherein each of the relief features has a height in a range from about 2 to 200 µm, and width in a range from about 20 to 200 µm. The kit for culturing cells further comprises a disposable housing pre-loaded with the carrier. The disposable housing may include, but is not limited to a bag, a flask, a tube, a petri dish, and a bottle. The kit may comprise the disposable housing as sterilized form for direct use. The carriers provided in the kit may also be sterilized and ready to use. In one example, the kit may further comprise appropriate media for growing cells. The media provided in the kit is sterilized and ready to use. The kit may comprise a manual or direction for users to use the carrier for growing or expanding cells in appropriate conditions.

An example of a method of making a carrier for growing cells, comprises providing a plurality of flat films and laminating the flat films to form a solid support. The solid support is subjected to a method such as embossing to generate indentations or relief features, in some other examples, casting, thermoforming, or injection molding achieved structured indentations or relief features. In some embodiments, the relief features may form on the carrier surface by punching holes in softened film followed by solidifying the film, depositing fibers on the surface onto an extruded film before solidification, depositing particles onto an extruded film before solidification, laminating a mesh on one or both sides of the carrier. In some examples, depositing fibers on the surface may include, but are not limited to, spraying fibers on the softened film, or by a nonwoven manufacturing process. In some embodiments, the solid support is embossed to form structured indentations and make an embossed solid support, which is further treated with a plasma to form a plasma treated embossed solid support, followed by cutting or dicing the plasma treated embossed solid support to a plurality of portions or pieces to form a plurality of carriers. In one example, the embossing of the solid support is performed by batch-stamping or hot embossing process using a mold. In one or more embodiments, a shaped die is used to form parallel ridges on the carrier surface. In this embodiment, embossing roll or mold is not used to form patterned structure for relief feature or indentations.

One example of a method of making a carrier for growing cells, comprises providing a polymer film, forming on the polymer film, on one or more sides, one or more relief features, imparting a surface treatment to at least a portion of the film comprising one or more of a corona discharge treatment, gas plasma treatment, chemical functionalization, coating or combinations thereof; and discretizing the treated polymer film into a plurality of portions.

Another example of a method for making the carriers comprises providing two flat polymer films. The method further comprises forming one or more relief features on the two flat polymer films individually on one surface of each of the two films, such as by embossing to make two embossed polymer films (embossed on one side each) to generate relief features on both sides, and laminating the two embossed polymer films together, back to back, to form a composite laminated embossed polymer film, so that the outwardly facing surfaces comprise one or more of the relief features. The laminated embossed polymer film may then be diced or otherwise separated into a plurality of portions; and imparting a treatment to the portions comprising one or more of corona discharge treatment, gas plasma treatment, chemical functionalization, coating or combinations thereof. To create relief features, the flat polymer films may alternatively be subjected to casting thermoforming or injection molding, or a bulk polymer may be made into a solution and cast on a mold to form a film with the relief features.

Another method of making a carrier with relief features for growing cells, comprises extruding polymeric resin and particle mixtures, forming a polymeric film with relief features that are formed by protruded particles, discretizing the polymeric film into a plurality of portions; and imparting a treatment to the portions comprising one or more of corona discharge treatment, gas plasma treatment, chemical functionalization or coating. The density of the polymeric film with embedded particles may be modified by embedding one or more particles with different density compared to the base film. The density may be specifically targeted to be matched or larger or smaller compared to culture media (density ~1 g/cc) to facilitate mixing or buoyancy of carriers or to facilitate settlement of the carriers.

The relief feature may be formed in the carrier by one or more of the following methods. In one example, a textured roll is used to make the relief features on a polymer film in a roll-to-roll process. The polymer film, textured roll, or both may be heated at the time of the process. In another example, a flat mold is prepared by cutting or machining the negative of the desired features into a metal block. The metal block then may be used as-is or replicated first as a positive and then as a negative, using, for example, a polymer casting process. The negative mold may then be used in a batch-stamping or hot embossing process to emboss the pattern into a polymer film. In another example, a mold thus formed may be used in a solvent-casting process to make the polymer film with the relief features. A polymer solution may be coated on to the mold or textured roll, and dried and/or cured. The dried/cured film then peeled off to yield a film with the desired relief features. Alternate methods such as thermoforming or injection molding may also be used.

One example of the method of making carriers in industrial scale, comprises various steps, as shown in FIG. 9. The polymer film is provided either from film extruder or roll of film (FIG. 9). Solid polymer resin 28 in the form of beads or pellets or powder are continuously fed into the twin-screw extruder 26 via feed 24, wherein the extruder comprises a motor 20 and gear box 22. The extruded film may be cooled using a cooling bath 32 and may be moved between or over rollers 34 that served to control the film tension. The film is softened as necessary for embossing by heat source 36 in the desired time frame. The heat source may be IR heater, quartz heater, flame or any type of heat source. For one example, quartz heater is used for heating film or roll. The heat source may not be necessary for the film continuously provided by extrusion process 30. Embossing is carried out by moving the softened film through the rolls 40 and 42 having a patterned surface. The two rolls apply pressure on the film when the film passes between them. The embossing surfaces contact the film at sufficient force to generate pattern on the surface of the film. The embossed film is then cooled 38 by any methods to reduce the temperature below the softening temperature in the desired time frame. The embossed roller forms a pattern of structured indentation or relief features on the surface. The cooling methods include cooling by blowing air or other gases, a water bath, chilled rollers, or cooling bath. Embossing is typically performed by a male pattern formed on a hard metal surface on an embossing roll. The metal surface can be nickel, copper, steel, and stainless steel. The pattern is typically machined onto the metal surface. A silicone rubber mold layer with male pattern can be utilized on the roll. The embossing may be carried out by several methods, including a continuous belt or sleeve. After embossing of the film, the patterned films are cooled 38 and pulled by using guide rolls 44. The patterned films are then discretized 46 into a plurality of portions to generate carriers followed by plasma treatment 48, and finally carriers are packaged and sterilized for further use 50. For one example, the patterned film can be wound in roll form and then discretized in a subsequent process.

A cell culture system of the invention uses one or more of the carriers for growing cells. In one embodiment, the cell culture system is a bioreactor, more specifically, an agitated bioreactor. A bioreactor refers to any device or system that supports cell growth in large scale culture. In one aspect, a bioreactor may refer to a device or a system for growing cells or tissues in the context of cell culture or tissue engineering. The bioreactor may employ agitation, generated by an internal impeller or paddle, or via externally rocking, rolling or shaking the culture vessel, or via bellows-induced motion of fluid. The bioreactor may, for example, be a reactor with rocking or rolling motion, such as wave motion reaction (for example, Wave Bioreactor™), a stirred tank bioreactor, a fluidized bed bioreactor, a fixed bed bioreactor, a roller bottle or airlift bioreactor.

A stirred tank bioreactor (STR) generally comprises an impeller system and optionally a sparging system to mix and aerate the culture. The principle of STR is mainly based on the stirring of an impeller to mix the fluid and aerate the culture well. In one or more embodiments, the STR comprises a magnetic stirrer as one of the components. The wave motion bioreactor comprises a rocking platform supporting a vessel containing a culture fluid, wherein the culture fluid comprises cells in a culture media. The rocking motion of the platform induces mixing and mass transport in the culture fluid. An airlift reactor relies on rising gas bubbles to mix and aerate the culture medium. Hydrodynamic factors such as mass transfer, mixing efficiency, and shear stress experienced by cells can be different in the different types of bioreactors. In addition, the cell growth rate and quality of cells may be influenced by operational differences between reactor types.

An example of a method of culturing adherent cells, comprises providing a carrier for growing cells, comprising one or more surfaces; where one or more relief features are present on one or more of the surfaces, wherein the carrier has a length at least about 0.2 mm, a width at least about 0.2 mm, and a height in a range from about 0.012 mm to 0.5 mm; and wherein each of the relief features/indentations has a height above the surfaces in a range from about 2 to 200 µm, and width in a range from about 20 to 200 µm; seeding the cells on the carrier surface and growing the cells.

In this example, the method of culturing adherent cells comprises providing one or more carriers for growing cells, adding an inoculum of cells to the carriers, allowing attachment of cells to the carriers, adding the carriers with inoculum in a bioreactor, adding culture medium, suspending the carriers in the medium continuously or intermittently, and allowing the cells to grow on the carriers. Cells may be grown in a culture flask prior to addition to the carriers. Cells may be grown on the carriers after extraction from a sample, for example, from blood, bone marrow or tissue section. In some other embodiments, the carriers may be introduced into a spinner flask, a stacked culture flask, a stirred tank reactor, a wave motion reactor or any other in-vitro cell culture system.

In one example of a method for culturing cells, comprises providing carriers for growing the cells, seeding of the cells to a disposable housing pre-loaded with the carriers, attaching the cells to the carriers with an agitation cycle, and growing the cells on the carrier in the same agitation cycle or a different agitation cycle. The disposable housing is pre-loaded with the carriers and sterilized before use. The cells are attached to the carriers using a cycle of agitation. The agitation may be intermittent agitation or continuous agitation. In some embodiments, the cells are grown on the carriers using the same cycle of agitation as used for attaching cells. In some other embodiments, the cells are grown on the carriers by using a different cycle of agitation. The cycle of agitation used for attaching cells to the carrier may be changed for growing various cells depending on the extent of agitation required for their growth.

Cultured cells may be detached or released from the carriers by a variety of methods. The cells may be released, for example, by using a mechanical method, an enzyme, a thermoresponsive polymer, a pH responsive polymer or a combination thereof. The cell release by mechanical method includes cell scraping. The cells may also be released by treating with proteolytic enzymes, such as trypsin. One non-enzymatic method uses calcium chelators, such as EDTA. Other non-enzymatic methods include, but are not limited to, physical methods that use ultrasound, which generates bubbles that facilitate cell detachment. Cultured cells from carriers comprising thermoresponsive polymers, such as poly-N-isopropylacrylamide (PNIPAAm) may be released by cooling the carrier to a temperature below lower critical solution temperature or LCST of the thermoresponsive polymer.

The carriers of the invention may be used for growing various adherent cells such as primary cells, stem cells and cell lines. The carriers may be commercially used for culturing cell lines. The cultured cells may be used for, but are not limited to, developing vaccines, overexpressing proteins, producing antibodies and combinations thereof. Non-limiting examples of cells are human mesenchymal stromal cells (hMSC), Chinese hamster ovary (CHO) cells, Madin-Darby canine kidney (MDCK) cells, and Vero cells. In one embodiment, the adherent cells are shear-sensitive cells such as hMSCs. The cells may be derived from human tissue, for example, from adipose tissue, bone marrow or cord blood. Culture and release of multipotent and pluripotent cells with high purity, high efficiency and high yield are a current research and clinical need.

The carriers can be used in combination with a bioreactor or culture vessel, to provide or enhance surface area for the attachment and growth of anchorage-dependent cells. Some embodiments of the kit of the invention for culturing cells comprise a disposable housing or vessel pre-loaded with one or more carriers. In one embodiment, the carriers and the disposable housing or vessel may be provided separately. In one embodiment, the housing may be reusable. The housing may be, for example, a bag, a flask, a tank, a tube, a petri dish or a bottle. The kit may further comprise culture media suitable for cell growth. The kit may comprise cells in a frozen condition and may further comprise a protocol for using the carriers.

Example 1

Fabrication of Carrier for Growing Cells Using Embossing Process

A pattern-master was prepared by cutting grooves in a flat aluminum block using a dicing saw, which was outfitted with a resin-bonded diamond blade. A set of parallel grooves (the term being interchangeably used with 'relief features') was cut in one direction, for ridge-like design (prototype 1). For post type of design (prototype 2), the holes on a flat aluminum block were drilled to desired depth and spacing using a micro-milling tool with the desired diameter. Finally, an effort was made to remove burrs that had formed in the first set of grooves during the cutting process or drilling process. After the grooves or holes were completed, the aluminum block was cleaned to remove any burrs on its surface. The pattern master determined the pattern geometry of the relief features.

A first-generation mold was then made from the pattern-master using a silicone rubber-molding compound, RTV 664 from Momentive Performance Materials. To produce the first-generation mold, the silicone compound was mixed at a 10:1 ratio according to directions from the manufacturer, using a Hauschild Speed Mixer. The pattern-master was placed in a hollowed-out Teflon block and uncured silicone compound was applied, in excess, across the surface of the pattern master. A chrome-plated steel plate was placed on top of the silicone, and the silicone was cured in a heated hydraulic press at 1000 lb force and 120° C. for 30 minutes. After cooling to room temperature, the cured silicone rubber first-generation mold was removed from the pattern-master. The first generation mold was coated with (tridecafluoro-1,1,2,2-tetrahydrooctyl)trichlorosilane by vacuum deposition at 750 mtorr for 45 minutes prior to making any second-generation molds. In some examples, the RTV silicone first-generation molds were replaced with fluorosilicone first-generation molds, by modifying the procedure by replacing the RTV 664 with a fluorosilicone and adjusting the mixing, process temperature, and process time accordingly. With fluorosilicone first generation molds, no coating was applied to the first generation mold prior to making second generation molds. Two second-generation molds were prepared using a silicone rubber-molding compound, RTV 664 (Momentive Performance Materials, Waterford, N.Y.) from the first-generation mold. The silicone compound was mixed at a 10:1 ratio according to directions from the manufacturer, using a Hauschild SpeedMixer. The first-generation mold was placed inside a steel frame with the patterned surface up and the silicone compound was dispensed, in excess, on the first-generation mold. A flat stainless steel plate was placed on top of the silicone and the silicone was cured in a heated hydraulic press at 1000 lb force and 120° C. for 30 minutes. After cooling to room temperature, the cured silicone rubber second-generation mold was removed from the fluorosilicone first-generation mold. Molds for cell carriers of different designs were made using the above fabrication procedures. The cell carriers of the invention may include relief features of different shapes, as determined by the pattern master and molds.

Multiple sheets of biaxially oriented polystyrene film (Trycite 1003U, Dow Chemical Company) were placed in between two second-generation molds with patterns facing in. The number of sheets of film was chosen so that the volume of polystyrene was sufficient to fill the pattern in the second-generation molds and still leave a small amount of polystyrene separating the molds. The films were then embossed in a heated hydraulic press with 1000 lb force and a temperature cycle that ramped up to 150° C. for 5 minutes and then cooled to below 60° C. The embossing process fused the multiple sheets of film into a single monolithic structure that replicated the texture of the molds and pattern-master on both sides. The embossed polystyrene film was removed from the molds after cooling to room temperature.

Example 2

Fabrication of Carrier for Growing Cells Using Film Extrusion Process

Particles, such as hollow glass spheres, solid glass spheres, and polystyrene beads were embedded in the film by extruding the particles and a polystyrene resin mixture. Particles were pre-mixed with polystyrene resin at desired concentration and fed into an extruder. The pre-determined amount of particles were added to the extruder so that the density of extruded film is not altered much from the polystyrene film formed from polystyrene resin, however sufficient particles were protruded on the surface, which generate the relief features.

In one example, a film with embedded hollow glass spheres (Prototype 3) was made by mixing 4 volume % of hollow glass spheres (25P45, Potters Industries LLC) of diameter 45 µm and density 0.25 g/cc, and ground polystyrene pellets (NOVA 1300, INEOS). The target density of the carrier was 1.01 g/cc. The mixed polystyrene and hollow glass spheres were fed into an extruder at 0.5 lb/hr, and the film was extruded at 200 rpm at the barrel temperature of 230° C. The 16 mm prism twin screw extruder (Prism TSE-16-TC, Thermo Electron Corporation) with an attached 3 inch wide film die was used to extrude the film. The extruded film was immediately cooled by air cooler and spooled in roll form. The die gap was set to be 0.508 mm, and the extruded film had a nominal thickness of 55 µm and a nominal base film thickness of 38 µm.

In another example, prototype 4 was made using solid glass spheres. Solid glass spheres of diameter 150-210 µm and density of 2.5 g/cc (Ballotini Impact Beads size #8, Potters Industries LLC) and polystyrene resin (NOVA 1300, INEOS) were used for Prototype 3. 1.7 volume % of the solid glass spheres were pre-mixed with the ground polystyrene pellets and fed into the Prism twin screw extruder to form the film. The extruded film had a nominal base film thickness of 38 µm and an overall film thickness of 200 µm including protruded particles. The density of the film was about 1.06 g/cc. The same extrusion processing conditions were used as for the hollow glass spheres.

In another example, prototype 5 was made using polystyrene beads. Polystyrene beads having diameter between 200-400 µm (Catalogue no. Nor2040, Norstone) were sieved and collected the beads with sizes less than 300 µm. The beads were washed using isopropyl alcohol and vacuum dried overnight at 80° C. 3 volume % of the beads were mixed with ground polystyrene (NOVA 1300, INEOS) and fed into the twin screw extruder to form a film. The same processing conditions were used as used for hollow spheres. The extruded film has a nominal base film thickness of 38 µm and 330 µm overall.

Example 3

Surface Treatment and Generating Plurality of Carriers

To make the polystyrene film with relief feature compatible with cell growth, the film was $O_2$ plasma treated using a Plasma Therm SLR vacuum plasma reactor. Plasma treatment was performed on each side of the embossed film for 1 minute at 100 mtorr pressure using 100 sccm (Standard Cubic Centimeters per Minute) $O_2$ flow and 100 W forward radio frequency (RF) power in reactive ion etching (RIE) mode.

Carriers for cell culture were prepared from the plasma-treated embossed sheets by manually cutting the film into 5 mm×5 mm pieces or 2 mm×2 mm pieces, or by discretizing and then sieving to select a particular size range, or by punching circular discs of the desired size or die-cutting by compressing the film under die-cutter using a hydraulic press.

Example 4

Large-Scale Fabrication of Carriers Using Roll-to-Roll Type Embossing Process Continuous roll-to-roll type embossing was performed by extrusion and calendering as shown in FIG. 9. Polystyrene (NOVA 1300, INEOS) film was extruded by a 16 mm twin screw extruder (Prism TSE-16-TC, Thermo Corporation) at 300 rpm, and feed rate of 4 lb/hr. The extruder barrel temperature was set at 240° C. The attached 3 inch wide film die was also set at 240° C. with die gap of 0.035 inch. The extruded film was continuously pulled using an 8 inch roll stack 34 (3 roll, Killion Extruders Inc.). The second-generation silicone molds with structured indentation were attached on two calender rollers (nip roll) 40 and 42 in the roll stack. The pattern was embossed on both sides of the film while the film was still formable/hot as it passed between the embossing rolls 40 and 42. The embossing roll pressure was set to be 40 psi, and the film was pulled at 5.4 ft/min. The embossing rolls were not heated and the heat source 36 was not used in this example. However, the rolls may be heated to facilitate the embossing process. The embossed film was then cooled by moving over chilled rolls 44 and spooled in roll form. The chilled roll was at room temperature without active cooling. The attached silicone pattern mold was 4 inch×4 inch and covered only a portion of the embossing rolls in this example. However, a larger mold can be attached on the embossing rolls to completely cover them. The embossed film was then treated for die-cutting using die-cutter 46, followed by plasma treatment of the carrier 48. The treated carriers finally packaged and sterilized 50 for further use for cell culture. FIG. 10 A shows the embossed pattern on the carriers by the process described above. The similar method may also be used to form the relief features on the carrier surface. The topography of FIG. 10 B was generated by chromatic white light profilometry and shows the structured indentation and regular height and intervals between each of the ridges.

Example 5

Cell Culture on the Carrier and Subsequent Cell Release

The carriers used for the following examples had a length and width of 5 mm, and a height of about 0.13 mm for Prototype 1 and about 0.33 mm for Prototype 5. The carriers comprised a plurality of relief features on each of the two outer surfaces. Each of the relief features had a height of 50 µm and width of 75 µm each for the ridge of Prototype 1 and a height of 100-200 µm for the protrusion of Prototype 5.

The carriers for cell culture were used for this example, to culture and release hMSC, although other cells may be cultured using these carriers, including but not limited to, CHO, MDCK, Vero, MSCs, embryonic stem cells, and adipose derived stem cells. These cells were routinely cultured on polystyrene surfaces using the following media: F-12K (Invitrogen) and 10% FBS (fetal bovine serum); and Eagle's minimum essential medium (EMEM, Invitrogen) and 10% FBS supplemented with 100 U/mL penicillin-streptomycin (P/S, Invitrogen). Culture methods were performed at 37° C., in a humidified atmosphere of 5% $CO_2$. Cells were passaged by performing the steps of briefly rinsing the cell layer with PBS (phosphate buffered saline) followed by addition of 3.0 ml of 0.25% (w/v) Trypsin and 0.53 mM EDTA solution to the culture flask and observing the cells in an inverted microscope until the cell layer is dispersed. Subsequently, 7 ml of complete growth medium was added to the cells and the media, and the cells were mixed by gently pipetting several times. Appropriate aliquots of the cell suspension were transferred to new culture vessels with fresh media.

Cells used in the following experiments were freshly pre-cultured and harvested from cell culture flasks after growing in incubators at 37° C. in a humidified, 5% $CO_2$ atmosphere. For static cell culture testing, pre-cultured cells were seeded at 2000 cells/$cm^2$ in 24-well plates with 1 mL growth medium per well. Tissue culture treated plates (TCPS surface, Nunc) and or non-adherent plates (Corning®) were used as control, wherein in the non-adherent plates (Corning®), disc-shaped embossed polystyrene carriers of the invention were inserted so as to fit snugly into the well. For cells grown under dynamic conditions on the carriers in stirred tank reactors (STR), pre-cultured cells were also seeded at 2000 cells/$cm^2$ in the carriers in 125 mL disposable spinner flasks (Corning®). Cells and carriers were agitated at 40 rpm on spinner bases connected to timers to regulate the agitation cycle. Cells were subjected to agitation continuously or intermittently. In intermittent conditions, for example, the agitator was turned on for 1 min, and off for 45 min per cycle.

Cells were washed with PBS and harvested by trypsin-EDTA (Invitrogen, ~10 minutes), when the cells were about 80-90% confluent. The trypsin was neutralized by addition of at least one volume of culture medium containing 10% serum, after the cells were released from the growth surface. After harvesting of the cells, cell number and cell viability were measured using a NucleoCounter® automated cell counter (ChemoMetec).

Example 6

Qualitative and Quantitative Estimation of Cell Growth

Cell staining and imaging—Samples for imaging were fixed at room temperature in 4% paraformaldehyde (PFA), which is freshly diluted in PBS from a 16% stock, stored in presence of argon in an amber glass vial. Once fixed, samples were stored at 4° C. until they were stained and imaged. Fixed cells were stained with Hoechst 33342 dye (from Invitrogen) to highlight the nuclei and with phalloidin-Alexa-568 (from Invitrogen) to visualize the cytoskeleton (actin) after permeabilization with 0.1% Triton X-100 detergent (Sigma). The stained cells were imaged with a Nikon Eclipse TE2000-U inverted fluorescence microscope, wherein the microscope was fitted with appropriate filter cubes and light source for the fluorophores being used.

Cell growth and morphology was assessed at intervals by taking samples of carriers and either measuring total ATP content or fixing and staining for fluorescence microscopy. Cell growth was assayed by CellTiter-Glo® luminescent cell viability assay reagent from Promega, which determines the number of viable cells in culture based on quantitation of the ATP present, which signals the presence of metabolically active cells. The process involves adding a single reagent (CellTiter-Glo®) directly to cells cultured in serum-supplemented medium. The homogeneous reagent results in cell lysis and generation of luminescent signal proportional to the amount of ATP present. The amount of ATP is directly proportional to the number of cells present in the culture. The assay relies on thermostable luciferase, which generates a stable 'glow type' luminescent signal resulting from oxyluciferin catalysed by luciferase in presence of $Mg^{+2}$, ATP, and molecular oxygen. After 10 minutes of the cell lysis, 200 µL aliquots of cell lysate were transferred to an opaque 96-well plate, mixed gently and read in a SpectraMax® luminescence microplate reader from Molecular devices to generate readings for cell viability. Luminescence readings from this assay are proportional to the number of viable cells present in the sample and so can be used to monitor the progress of cell growth.

Example 7

Quantitative Estimation of Human Mesenchymal Stromal Cell (hMSC) Growth

The hMSCs used for this experiment were purchased from Lonza Inc. (Part number PT-2501) (Basel, Switzerland). The hMSCs were grown on the carrier in stirred tank reactors (STR). The cell growth was monitored via CellTiter-Glo® measurements and qualitatively via imaging. The growth rate of hMSCs on carriers in STR is comparable with that on TCPS, as shown in FIG. 5. Luminescence of the cells represents cell number, and the luminescence increases with increasing cell count over time. FIG. 5 shows the growth of hMSCs on ridge design carriers, on MicroHex™ carriers using STR and on tissue culture treated plate surface (TCPS) in static culture. The graphs clearly indicate a uniform cell growth over time in culture using carriers with relief features formed with solid glass spheres (prototype 4) and polystyrene beads (prototype 5) compared to MicroHex™ as a control. Cells were observed to grow on both surfaces of the carriers. Cells were grown on carriers in spinner flasks from Corning Life Sciences. Cells were grown on tissue culture polystyrene (TCPS) in static medium as a positive control.

Example 8

Characterization of hMSC Growth on Carriers with Various Relief Features

To demonstrate that the carriers support the growth of hMSCs, carriers were procured with two different types of relief features. One type of carrier comprised relief features having ridge-like structure (Prototype 1). The other types of relief features were made of glass beads in a polystyrene film (prototype 4) and polystyrene beads in a polystyrene film (Prototype 5), wherein the polystyrene beads have diameter of about 200 µm. FIG. 5 demonstrates robust hMSC cell growth on the carrier of Prototype 4 and on Prototype 5 design of relief features using STR; the growth is comparable to the cells grown on MicroHex™ as a control and on TCPS under static conditions.

Example 9

Characterization of hMSC Growth in Larger Scale Culture

The hMSC culture was scaled up in 1 L spinner flask with 500 ml of media. FIG. 6 shows robust hMSC (Lonza) growth on Prototype 1 (relief feature with the ridge structure) after 1 day, 5 days, and 7 days as shown in FIG. 6(A), FIG. 6 (B), and FIG. 6 (C) respectively. FIGS. 7 (A) and 7 (B) show hMSC cell growth on Prototype 5, wherein the particles shown in the image are embedded in the polystyrene film (relief feature) of prototype 5. FIGS. 7 (A) and 8(A) show the hMSCs (Lonza) growth after day 1 and day 6, respectively. The prototype 5, which is a polymeric film comprising polystyrene beads with 200 micron diameter, was tested in 250 ml spinner with 100 ml of media.

Example 10

Characterization of Carrier Stacking During Cell Growth

Figure 8B:
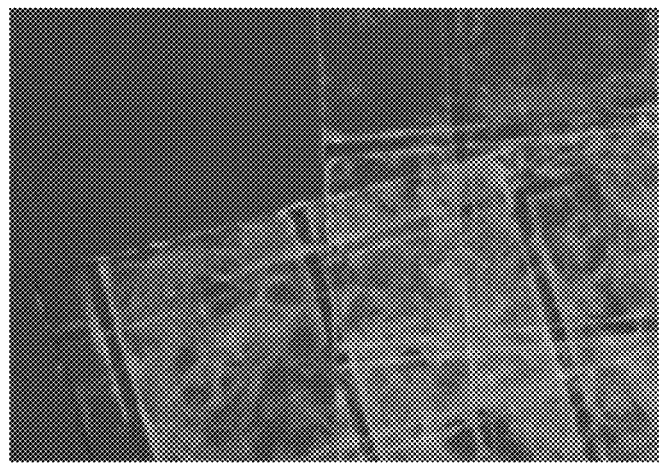
Figure 8C:
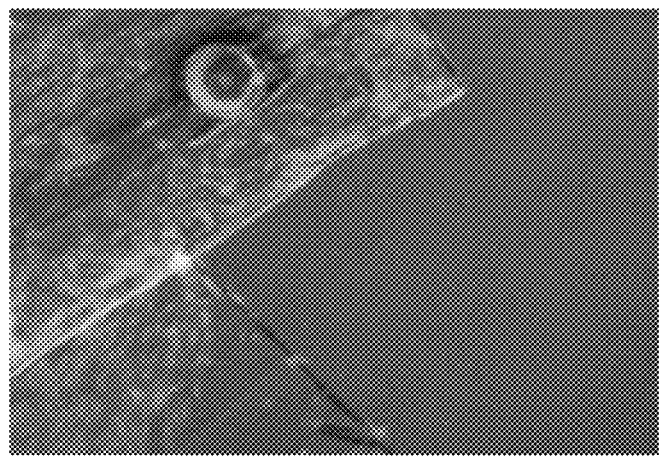

As cells grow, cells start to bridge carriers and eventually large stacks of the carriers are formed where each of the carriers is physically connected to other. Clumping of MicroHex™ carriers during cell growth after 7 days of culture is shown in FIG. 8 (A). Carriers with relief features did not show physical connection between two or more carriers. For example, the carriers comprising parallel ridges used for growing hMSC and after cell growth, the carriers did not show formation of clumps. The images of FIGS. 8(B) and 8(C) show overlapped carriers with relief features for prototype 1 after 7 days of culture and for prototype 5 after 6 days of culture.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A method of culturing adherent cells, comprising:
providing a carrier for growing the cells, comprising a first surface and a second surface opposing the first surface; and one or more relief features on the first surface and the second surface, the relief features on the first surface and the second surface comprising discontinuous protrusions that are positioned away from an edge of the carrier, wherein the carrier has a length in a range from about 0.2 mm to 25 mm, a width in a range from about 0.2 mm to 25 mm, and a height in a range from about 0.012 mm to 0.5 mm; and wherein each of the relief features has a height above the surfaces in a range from about 2 to 200 µm, and width in a range from about 20 to 200 µm and wherein the relief features on the first surface and the second surface comprise discontinuous protrusions that are positioned away from an edge of the carrier.

2. The method of claim 1, wherein the relief features prevent clumping of two or more carriers while growing the cells.

3. The method of claim 1, further comprising growing the cells on the carrier in a bioreactor.

4. The method of claim 3, wherein the bioreactor comprises fluid having a forced convective fluid motion.

5. The method of claim 3, wherein the bioreactor is a stirred tank bioreactor, a reactor with rocking or rolling motion, a reactor with packed bed or a reactor with fluidized bed.

6. The method of claim 3, wherein the bioreactor is a stirred tank bioreactor.

7. The method of claim 3, wherein the bioreactor comprises a disposable housing comprising fluid.

8. The method of claim 7, further comprising loading the carriers to the disposable housing for growing cells.

9. The method of claim 7, wherein the disposable housing is a bag, a flask, a tube, a petri dish, or a bottle.

10. The method of claim 7, wherein the relief features prevent sticking of one or more carriers to one or more walls of the disposable housing.

11. The method of claim 1, wherein the relief features decrease stacking of two or more carriers.

12. The method of claim 1, wherein the cells are growing at a temperature in a range of 30° C. to 37° C.

13. The method of claim 1, wherein the cells are released after growing on the carrier using a mechanical method, a chelant, an enzyme, a thermoresponsive coating, a pH responsive coating, or a combination thereof.

14. The method of claim 13, wherein the cells are released after growing on the carrier using a thermoresponsive polymer coating.

15. The method of claim 14, wherein the cells are released at a temperature below lower critical solution temperature (LCST) of the thermoresponsive polymer.

16. The method of claim 1, wherein the cells are human mesenchymal stromal cells (hMSC), Chinese hamster ovary (CHO) cells, Madin-Darby canine kidney (MDCK) cells, or Vero cells.

17. The method of claim 1, wherein the relief features disposed on the first surface comprise protrusions having a first shape, and wherein the relief features disposed on the second surface comprise protrusions having a second shape.

18. The method of claim 1, wherein the relief features disposed on the first surface and the second surface comprise protrusions having rotational symmetry about an axis orthogonal to a plane of the carrier.

19. The method of claim 1, wherein the relief features comprise profiled post protrusions that narrow as they extend away from the surface of the carrier.

20. The method of claim 1, wherein the relief features comprise domed protrusions.

21. The method of claim 1, wherein the relief features comprise cylindrical post protrusions.

22. The method of claim 1, wherein the relief features disposed on the first surface comprise protrusions oriented along a first axis, and wherein the relief features disposed on the second surface comprise protrusions oriented along a second axis.

23. A method of culturing adherent cells, comprising:
providing a carrier for growing the cells, comprising a first surface and a second surface opposing the first surface; and one or more relief features are present on the first surface and the second surface, wherein the relief features disposed on the first surface comprise protrusions having a first shape, and wherein the relief features disposed on the second surface comprise protrusions having a second shape, wherein the carrier has a length at least about 0.2 mm, a width at least about 0.2 mm, and a height in a range from about 0.012 mm to 0.5 mm; and wherein each of the relief features has a height above the surfaces in a range from about 2 to 200 µm, and width in a range from about 20 to 200 µm;
seeding the cells on the first surface and the second surface of the carrier;
loading the carrier to a disposable housing comprising fluid;
loading the disposable housing to a bioreactor; and
growing the cells on the carrier in the bioreactor.

24. The method of claim 23, wherein the disposable housing is a bag, a flask, a tube, a petri dish, or a bottle.

25. The method of claim 23, wherein the relief features reduce clumping of two or more of the carrier or sticking of one or more carrier to one or more walls of the disposable housing.

26. The method of claim 23, wherein the fluid have a forced convective fluid motion.

27. The method of claim 23, wherein the bioreactor is a stirred tank bioreactor, a reactor with rocking or rolling motion, a reactor with packed bed or a reactor with fluidized bed.

28. The method of claim 23, wherein the bioreactor is a stirred tank bioreactor.

* * * * *